United States Patent
Krupa et al.

(10) Patent No.: US 8,801,253 B2
(45) Date of Patent: Aug. 12, 2014

(54) ILLUMINATION DEVICE

(75) Inventors: Robert J. Krupa, Leominster, MA (US); Thomas V. Root, Beverly, MA (US)

(73) Assignee: Optim LLC, Sturbridge, MA (US)

( * ) Notice: Subject to any disclaimer, the term of this patent is extended or adjusted under 35 U.S.C. 154(b) by 0 days.

(21) Appl. No.: 12/251,824

(22) Filed: Oct. 15, 2008

(65) Prior Publication Data

US 2009/0034286 A1 Feb. 5, 2009

Related U.S. Application Data

(63) Continuation of application No. 11/323,481, filed on Dec. 30, 2005, now Pat. No. 7,798,692, which is a continuation-in-part of application No. 10/810,504, filed on Mar. 26, 2004, now Pat. No. 7,229,201.

(60) Provisional application No. 60/457,672, filed on Mar. 26, 2003.

(51) Int. Cl.
*F21V 7/10* (2006.01)

(52) U.S. Cl.
USPC ............ 362/556; 362/555; 385/121; 385/901

(58) Field of Classification Search
USPC ......... 362/551, 554, 555, 556, 572, 573, 574, 362/612, 613, 615, 616, 617, 621, 800; 250/227.24; 257/79, 81, 82, 88, 94, 98; 385/34, 88–94, 115–117, 119, 120, 385/121, 901
See application file for complete search history.

(56) References Cited

U.S. PATENT DOCUMENTS

| 2,235,979 | A | | 3/1941 | Brown | |
| 3,756,688 | A | * | 9/1973 | Hudson et al. | 385/43 |
| 3,832,028 | A | | 8/1974 | Kapron | |
| 4,101,197 | A | * | 7/1978 | Kent et al. | 385/90 |
| 4,212,021 | A | * | 7/1980 | Ono et al. | 257/94 |
| 4,241,978 | A | | 12/1980 | Dubois et al. | |
| 4,281,891 | A | | 8/1981 | Shinohara et al. | |
| 4,385,344 | A | | 5/1983 | Gonser | |
| 4,763,975 | A | | 8/1988 | Scifres et al. | |
| 4,836,782 | A | * | 6/1989 | Gonser | 433/229 |
| 5,065,011 | A | * | 11/1991 | Fujihara et al. | 250/227.24 |
| 5,098,292 | A | * | 3/1992 | Lazarof | 433/141 |
| 5,107,537 | A | | 4/1992 | Schricks et al. | |

(Continued)

FOREIGN PATENT DOCUMENTS

| DE | 202 11713 | 11/2002 |
| EP | 1396754 | 3/2004 |

(Continued)

OTHER PUBLICATIONS

The International Search Report and Written Opinion for International Application No. PCT/US2010/021567, Date of Mailing Apr. 16, 2010 (11 pages).

(Continued)

*Primary Examiner* — Hargobind S Sawhney
(74) *Attorney, Agent, or Firm* — Proskauer Rose LLP

(57) ABSTRACT

Illumination devices include a light source including a substantially planar light-emitting surface and an optical rod or optical taper disposed proximate to the substantially planar light-emitting surface to optically couple the optical rod and the substantially planar light-emitting surface.

16 Claims, 5 Drawing Sheets

(56) References Cited

U.S. PATENT DOCUMENTS

| | | | |
|---|---|---|---|
| 5,271,079 A * | 12/1993 | Levinson | 385/46 |
| 5,290,169 A | 3/1994 | Friedman et al. | |
| 5,341,445 A | 8/1994 | Davenport et al. | |
| 5,420,768 A * | 5/1995 | Kennedy | 362/119 |
| 5,537,503 A | 7/1996 | Tojo et al. | |
| 5,586,207 A * | 12/1996 | Goodwin | 385/92 |
| 5,631,987 A | 5/1997 | Lasky et al. | |
| 5,634,711 A * | 6/1997 | Kennedy et al. | 362/119 |
| 5,680,492 A | 10/1997 | Hopler et al. | |
| 5,687,270 A * | 11/1997 | Takizawa | 385/94 |
| 5,718,664 A | 2/1998 | Peck et al. | |
| 5,761,364 A * | 6/1998 | Knapp et al. | 385/123 |
| 5,764,845 A | 6/1998 | Nagatani et al. | |
| 5,803,729 A * | 9/1998 | Tsimerman | 433/29 |
| 5,888,194 A | 3/1999 | Utsumi et al. | |
| 5,967,653 A * | 10/1999 | Miller et al. | 362/580 |
| 5,975,895 A | 11/1999 | Sullivan | |
| 6,092,935 A * | 7/2000 | Althaus et al. | 385/93 |
| 6,159,005 A * | 12/2000 | Herold et al. | 433/29 |
| 6,260,994 B1 | 7/2001 | Matsumoto et al. | |
| 6,318,887 B1 | 11/2001 | Matsumoto | |
| 6,331,156 B1 | 12/2001 | Haefele et al. | |
| 6,436,035 B1 * | 8/2002 | Toth et al. | 600/249 |
| 6,438,302 B1 | 8/2002 | Utsui et al. | |
| 6,547,400 B1 | 4/2003 | Yokoyama | |
| 6,554,456 B1 | 4/2003 | Buelow et al. | |
| 6,572,280 B2 * | 6/2003 | Hurt et al. | 385/92 |
| 6,692,251 B1 * | 2/2004 | Logan et al. | 433/29 |
| 6,692,431 B2 | 2/2004 | Kazakevich | |
| 6,776,537 B2 * | 8/2004 | Toyama | 385/93 |
| 6,832,849 B2 | 12/2004 | Yoneda et al. | |
| 6,918,693 B2 | 7/2005 | Ota et al. | |
| 6,921,920 B2 | 7/2005 | Kazakevich | |
| 6,932,599 B1 | 8/2005 | Hartung | |
| 6,950,573 B2 | 9/2005 | Ota et al. | |
| 6,963,688 B2 | 11/2005 | Nath | |
| 7,063,450 B2 | 6/2006 | Ehara et al. | |
| 7,182,597 B2 * | 2/2007 | Gill et al. | 433/29 |
| 7,300,175 B2 | 11/2007 | Brukilacchio | |
| 7,645,056 B1 * | 1/2010 | Mills et al. | 362/294 |
| 7,762,950 B2 | 7/2010 | Hirata | |
| 7,798,692 B2 | 9/2010 | Krupa et al. | |
| 7,902,560 B2 | 3/2011 | Bierhuizen et al. | |
| 2002/0120181 A1 | 8/2002 | Irion | |
| 2003/0141507 A1 | 7/2003 | Krames et al. | |
| 2003/0156430 A1 | 8/2003 | Ota et al. | |
| 2003/0201462 A1 | 10/2003 | Pommer et al. | |
| 2003/0231843 A1 | 12/2003 | Colombo et al. | |
| 2003/0235800 A1 | 12/2003 | Qadar | |
| 2004/0004846 A1 | 1/2004 | Steen et al. | |
| 2004/0049172 A1 | 3/2004 | Root et al. | |
| 2004/0052485 A1 | 3/2004 | Van Eijkelenborg et al. | |
| 2004/0091219 A1 | 5/2004 | Christensen et al. | |
| 2004/0246744 A1 | 12/2004 | Krupa et al. | |
| 2005/0243570 A1 | 11/2005 | Chaves et al. | |
| 2005/0265653 A1 | 12/2005 | Cai et al. | |
| 2006/0158896 A1 | 7/2006 | Krupa et al. | |
| 2006/0171693 A1 | 8/2006 | Todd et al. | |
| 2007/0086205 A1 | 4/2007 | Krupa et al. | |
| 2007/0274096 A1 | 11/2007 | Chew et al. | |
| 2008/0029720 A1 | 2/2008 | Li | |
| 2009/0122573 A1 | 5/2009 | Krupa et al. | |
| 2009/0185392 A1 | 7/2009 | Krupa et al. | |
| 2009/0190371 A1 | 7/2009 | Root et al. | |

FOREIGN PATENT DOCUMENTS

| | | |
|---|---|---|
| GB | 1409793 | 10/1975 |
| JP | 5264871 | 10/1993 |
| JP | 5313045 | 11/1993 |
| WO | 99/16136 | 4/1999 |
| WO | 2005/103562 | 11/2005 |
| WO | 2006/034171 | 3/2006 |

OTHER PUBLICATIONS

Non-Final Office Action for U.S. Appl. No. 12/349,908. Mailing date: Nov. 9, 2009, 8 pages.
International Search Report for PCT Application No. PCT/US2009/032050 mailed on Jul. 10, 2009 (3pg).
Non-Final Office Action for U.S. Appl. No. 12/360,027. Mailing date: May 31, 2011, 21 pages.
Response to Non-Final Office Action for U.S. Appl. No. 12/360,027, dated Nov. 30, 2011, 16 pages.
Final Office Action for U.S. Appl. No. 11/323,481, dated Nov. 13, 2009, 15 pages.
Final Office Action for U.S. Appl. No. 11/323,481, dated Oct. 14, 2008, 15 pages.
Non-Final Office Action for U.S. Appl. No. 11/323,481, dated Dec. 28, 2007, 12 pages.
Non-Final Office Action for U.S. Appl. No. 11/323,481, dated Jan. 13, 2009, 14 pages.
International Search Report for PCT Application No. PCT/US2005/033435 mailed on Jan. 27, 2006 (2 pgs).
International Search Report for PCT Application No. PCT/US2006/048427 mailed on Apr. 27, 2007 (3 pgs).

* cited by examiner

ILLUMINATION DEVICE

RELATED APPLICATIONS

This application is a continuation application of U.S. patent application Ser. No. 11/323,481 filed on Dec. 30, 2005. U.S. patent application Ser. No. 11/323,481 is a continuation-in-part of U.S. patent application Ser. No. 10/810,504 filed on Mar. 26, 2004, which claims the benefit of U.S. Provisional Application No. 60/457,672, filed on Mar. 26, 2003. The entire disclosure of each of the above-referenced applications is incorporated herein by reference.

FIELD OF THE INVENTION

This invention relates to an illumination device including a substantially planar light-emitting surface coupled to an optical rod or optical taper.

BACKGROUND OF THE INVENTION

Advances in light source technology, such as, for example, light-emitting diode (LED) technology, have led to very bright and reliable solid state lamps. However, challenges remain with respect to coupling LEDs to optical transmission media, such as, for example, optical rods and optical tapers. While there have been numerous attempts to utilize low power (<1 W electrical power consumption, typically operating below 100 mW) light-emitting diodes (LEDs) coupled to fiber optic light guides or other optical devices as light sources for endoscopy, dentistry, and for remote illumination of objects (as with a flashlight, head light, or lamp), most of these prior attempts have employed numerous low power LEDs for remote illumination. Generally, multiple LEDs are necessary because the light output from a single, low power LED is typically too weak to properly illuminate an object. In addition, the arrangement of the multiple LEDs to the optical transmission media used in these prior attempts has resulted in unacceptable light loss, thereby further decreasing the low power LED's ability to properly illuminate an object.

SUMMARY OF THE INVENTION

In general, the present invention relates to increasing the amount of light transmitted through an illumination device by means of an inventive coupling approach between a light source and an optical rod or optical taper. In some embodiments, the invention further relates to an endoscope (e.g., medical or industrial) including the inventive coupling approach, a lamp including the inventive coupling approach, or a head light including the inventive coupling approach. Certain embodiments of the present invention, utilize a high power LED, (i.e., an LED having a power consumption between about 1 to 5 W).

In one aspect, the invention relates to an illumination device, such as, for example, an endoscope, a lamp, or a head light. The illumination device includes a light source including a substantially planar light-emitting surface and an optical rod or optical taper disposed proximate to the substantially planar light-emitting surface. By arranging the optical rod or optical taper in a proximate relationship to the substantially planar light-emitting surface, the two elements are coupled in a manner which allows a large amount of the light emitted by the light source to be transmitted directly into the optical rod or optical taper. As a result, a greater amount of light from the light source can be transmitted through the illumination device and onto an object for illumination. Embodiments of the present invention do not include auxiliary optics, such as lenses or mirrors, disposed between the light source and the optical rod or optical taper, but instead rely on the close placement (e.g., direct contact or close proximity) of the optical rod or taper to the planar light-emitting region of the light source. The lack of auxiliary optics between the light source and the optical rod or optical taper simplifies the mechanical design and space requirements for the illumination device. As a result, illumination devices in accordance with the presence invention, can be small and compact while providing the desired illumination strength.

Embodiments of this aspect of the invention can include one or more of the following features. The substantially planar light-emitting surface can include an emitting surface of a light-emitting diode chip. In some embodiments, the substantially planar light-emitting surface can include the surface of a light-emitting diode chip that has been coated with a film of a substance that emits light when the light-emitting diode chip is activated (e.g., a phosphor film coating the surface of the chip). In certain embodiments, the substantially planar light-emitting surface comprises a transparent substantially planar window disposed over an emitting surface of a light emitting diode chip. For example, in some embodiments, the window can be disposed directly over a LED chip. In other embodiments, the window can be disposed over a phosphor coated LED chip. The substantially planar light-emitting surface can be in direct contact with the optical rod or optical taper. In some embodiments an adhesive or index matching material (e.g., a coupling gel) can be disposed between the optical rod or optical taper and the substantially planar light-emitting surface. In certain embodiments, the optical rod or taper is disposed proximate to but not in direct contact with the substantially planar light-emitting surface. As a result, a gas is disposed between the optical rod or optical taper and the substantially planar light-emitting surface.

Other embodiments of this aspect of the invention can include one or more of the following features. The optical rod can be formed of a clad rod, a silvered rod, an aluminized rod, or a fiber bundle. The optical rod can have a first end that is proximate to the substantially planar light-emitting surface and a second end that is proximate to a light guide. The optical taper can include a first end that has a smaller surface area than a second end of the optical taper. In some embodiments, the first end (i.e., with the smaller surface area) can be in direct contact with the substantially planar light-emitting surface of the light source. In other embodiments, the second end (i.e., with the larger surface area) can be in direct contact with the substantially planar light-emitting surface of the light source. The optical taper can be formed of a glass optical taper, a plastic optical taper, or a plurality of fibers. While one end of the optical rod or optical taper is proximate to the substantially planar light-emitting surface, the other end of the optical rod or taper can be connected to a light guide. In some embodiments, a light post taper can be disposed between the optical rod or the optical taper and the light guide.

In another aspect, the invention is directed to a method of collimating light from a light source. The method includes attaching an optical rod or optical taper to a substantially planar light-emitting surface of the light source and activating the light source.

In another aspect, the invention is directed to a method of illuminating an object. The method includes providing a device including a light source having a substantially planar light-emitting surface and an optical rod or taper having a first end held proximate to the substantially planar light-emitting surface; positioning the device relative to the object; and activating the light source. In some embodiments, the optical rod or taper can include a second end attached to optics to transmit the light emitted from the light source through the optical rod or taper to the object.

Any of the above implementations can realize one or more of the following advantages. The illumination devices and methods described above are efficient at transmitting light from the light source into the optical rod or optical taper. As a result, objects can be illuminated with a proper amount of light (e.g., object is visible under endoscopic examination, object under a lamp is sufficiently lighted for viewing purposes). Another advantage realized in the above embodiments is that the optical rod or optical taper can be coupled to the light source without the use of additional optical components or auxiliary optics, such as, for example, mirrors, lenses, reflectors. As a result, a large amount of the light emitted by the light source can be coupled directly into the optical rod or optical taper, thereby allowing a greater amount of light from the light source to be transmitted to the objects under investigation. The lack of auxiliary optics between the light source and the optical rod or taper also simplifies the mechanical design and size of the illumination device. In addition, the high light output and high coupling efficiency of the light emitted by the light source into the optical rod or optical taper increases battery lifetime and thus permits the use of smaller capacity, and smaller volume batteries to power the illumination device.

BRIEF DESCRIPTION OF THE DRAWINGS

The foregoing and other features and advantages of the present invention, as well as the invention itself, will be more fully understood from the following description of various embodiments, when read together with the accompanying drawings.

DETAILED DESCRIPTION

Figure 1:
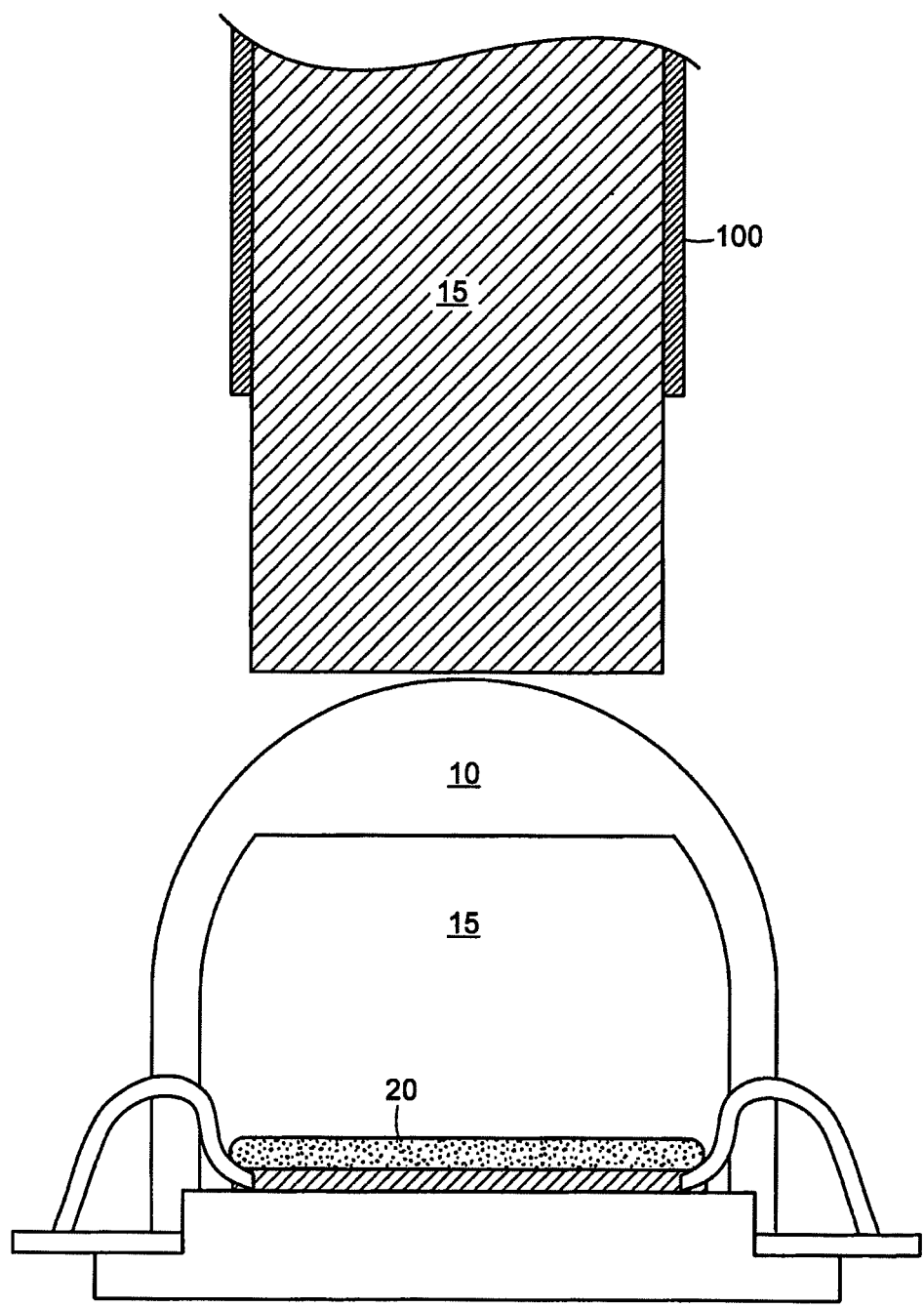
FIG. 1 is an illustration of a prior art illumination device including a LED-based light source.

Prior art illumination devices, such as, for example, the illumination device shown in FIG. 1, include a light source 5 having a dome-shaped lens 10 optically coupled to transmission media 15. With this coupling arrangement, light is ineffectively transmitted to the transmission media 15 because the light emitting portion 20 of the light source 5 is not sufficiently close to the transmission media 15 (i.e., due to the curvature of the dome lens 10, the light emitting portion 20 is spaced at an unacceptable distance away from the transmission media). In addition, the dome shape lens 10 provides a convex light-emitting surface. As a result, a portion of the light passing through an interface between the light source 5 and the transmission media 15 is lost, thereby decreasing the light strength and efficiency of conventional illumination devices.

Illumination devices of the present invention include a substantially planar light-emitting surface which is proximate to either an optical rod or an optical taper. As a result, a greater amount of light is transmitted from the light source to the optical rod or taper than in prior art systems.

Figure 2:
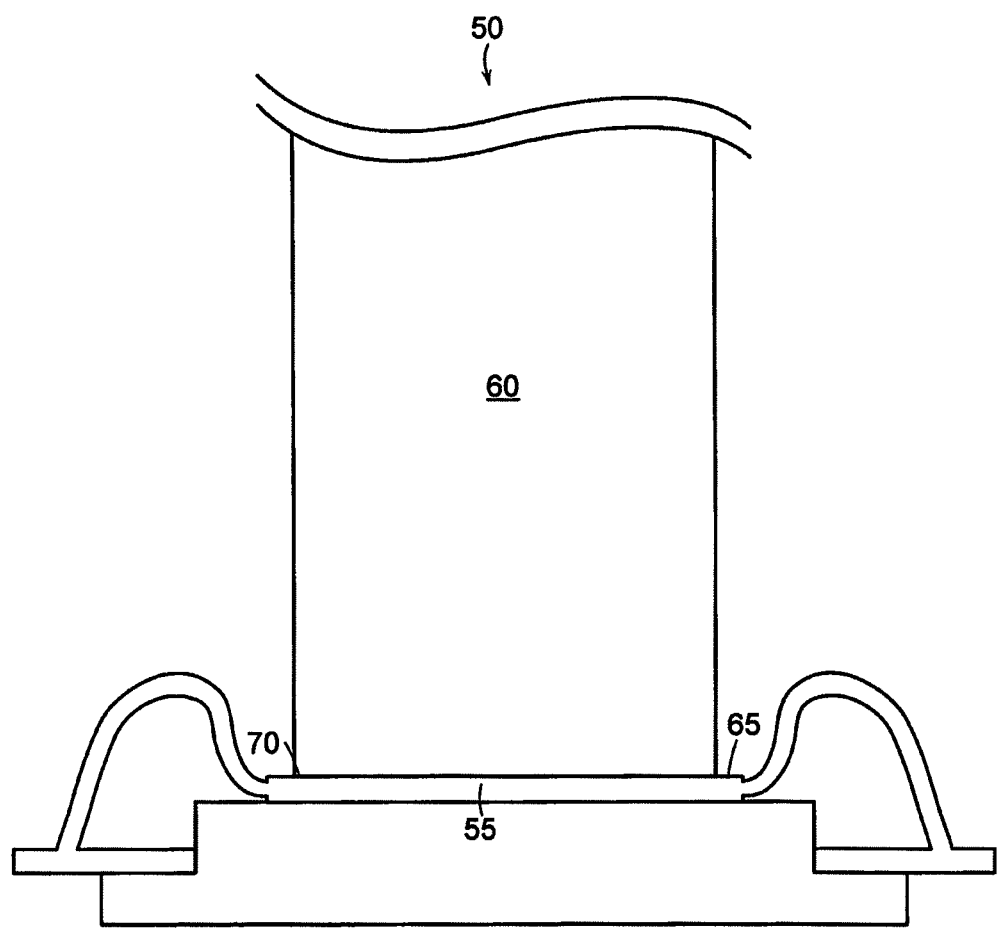
FIG. 2 is an illustration of an illumination device including a substantially planar light-emitting surface in accordance with the present invention.

In accordance with one embodiment of the invention, an illumination device 50 shown in FIG. 2 includes a LED 55, such as, for example, a high power LED (Luxeon III Model LXHL-LW3C, Lumileds Lighting, San Jose, Calif.) and an optical rod 60. A dome lens, such as the dome lens 10 shown in FIG. 1, and any index matching material surrounding the LED 55 was not employed or was removed prior to coupling the LED 55 to the optical rod 60. As a result, the substantially planar light-emitting surface 65 of the LED 55 (e.g., the surface of a light-emitting chip in the LED 55) is proximate to a first end 70 of the optical rod 60. The substantially planar light-emitting surface 65 and the first end 70 together form a planar interface in which light can be transmitted with less light loss than in an interface including a curved or convex surface.

Figure 3:
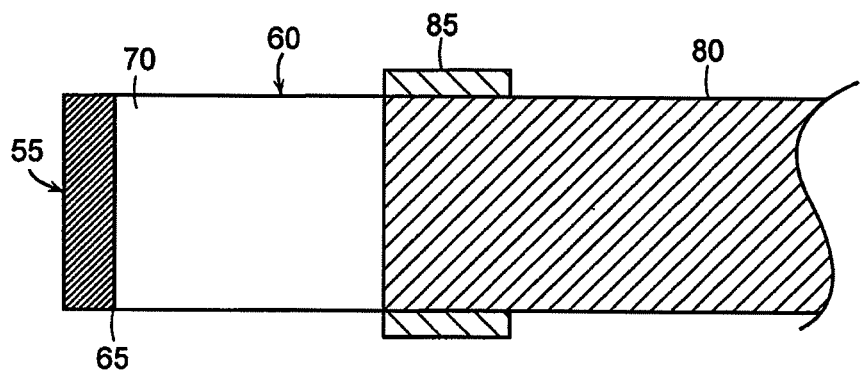
FIG. 3 is an illustration of another embodiment of an illumination device including a substantially planar light-emitting surface in accordance with the present invention.

The coupling arrangement of the light source 55 and the optical rod 60 provides many advantages to the illumination device 50 over prior art systems. Besides an increase in the amount of light transmitted through the illumination device, the coupling arrangement shown in FIG. 2 provides light source protection and mechanical stability to the illumination device 50. Specifically, the optical rod 60 protects the LED 55 from the external environment and also provides an additional advantage of being a rugged element to which additional elements of the illumination device can be easily coupled to. For example, referring to FIG. 3, a light guide bundle 80 formed of a plurality of optical fibers and held together by a ferrule 85 can easily be attached to the optical rod 60 without fear of damaging the light-emitting diode.

Figure 4:
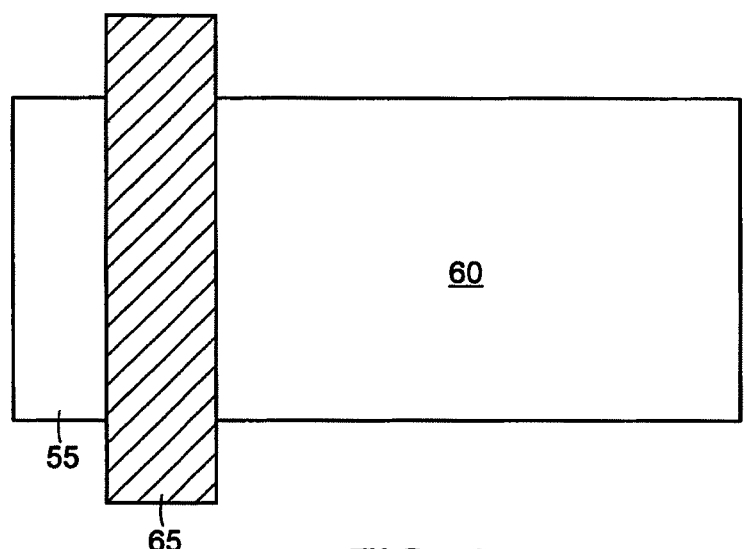
FIG. 4 is an illustration of another embodiment of an illumination device including a substantially planar light-emitting surface in accordance with the present invention.

The substantially planar light-emitting surface 65 of the LED 55 is the top surface of the LED chip. In some embodiments, the substantially planar light-emitting surface 65 can further include a coating of a substance that emits white light or one or more specific colors of light when activated. For example, the substantially planar light-emitting surface 65, in certain embodiments, includes a phosphor film or coating on the top surface of the LED 55. In other embodiments, such as the embodiments shown in FIG. 4, the substantially planar light-emitting surface 65 can be formed of a transparent flat window placed over the LED 55. In this embodiment, light is emitted from the top surface of the LED 55 and then through the transparent window. The flat window is proximate to the optical rod 60 and forms a planar interface with the optical rod.

Optical rod 60 can be formed from a transparent material or any material which allows light to pass through. Examples of materials that can be used to form the optical rod include glass, plastic, and sapphire. In addition, the optical rod can be a clad rod, a silvered rod, an aluminized rod, or formed form a plurality of fibers (e.g., fiber bundle).

Figure 5:
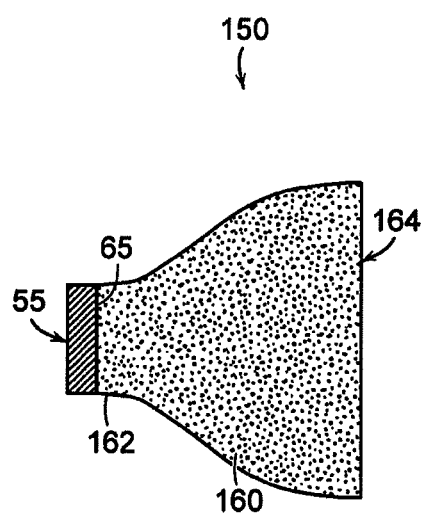
FIG. 5 is an illustration of another embodiment of an illumination device including a substantially planar light-emitting surface in accordance with the present invention.

Referring to FIG. 5, illumination device 150 includes LED 55 and an optical taper 160 positioned proximate to the substantially planar light-emitting surface 65 of the LED 55. Optical taper 160 is formed from any transparent material such as, for example, glass or plastic and has a first end or a smaller surface area end 162 and a second end or a larger surface area end 164. The optical taper 160 can be made from a solid rod of transparent material that is drawn down to a smaller diameter or profile at one end or, in other embodiments, the optical taper can be formed from a plurality of fibers (e.g., a fiber taper) that are also drawn down in diameter or profile. The optical taper 160 provides the advantage of resizing and reshaping the output of the light from the light source (e.g., LED 55). For example, a typical LED die is about 1 mm×1 mm square that emits over a broad angular cone. Employing a high index of refraction transparent material, such as, for example glass or plastic, in the taper 160 produces a high acceptance angle of light at the first end or smaller surface area end 162 of the taper. The larger surface area end 164 of the taper exhibits a reduction in the numerical aperture (NA) by the ratio of the end diameters. For example, a 1:3 taper made from glass has an angular aperture at the first end 162 of 123 degrees and a numerical aperture of 0.88 NA. The second end 164 of the taper has a numerical aperture of 0.29 NA and an angular aperture of 34 degrees. As a result, the taper 160 provides a number of advantages to the illumination device 150. For example, in the embodiment shown in FIG. 5, the taper 160 collects a very large solid angle of light emitted by the LED 55 because of the high NA at the first end 162 of the taper. The taper 160 protects the LED 55 from the environment. The taper 160 collimates the light as it passes through the taper 160 and delivers the light in a manner that is more readily coupled to light guides. The taper 160 presents a lower dispersion of light to additional optics should imaging or collection of the light be necessary for a particular application, such as, for example, spot light imaging in a museum or projection of a transparency image. In addition, the taper 160 provides mechanical stability to illumination device 150 and is a rugged element to which additional elements of the illumination device can be easily coupled to.

While the taper 160 as shown in FIG. 5 has its first end 162 in direct contact with the LED 55, other resizing and reshaping arrangements are available. For example, instead of the small surface area end 162 being in contact with the planar light-emitting surface 65 of the LED 55, the larger surface area 164 can be in contact with the light-emitting surface 65. This embodiment allows for a smaller angle of light to be collected from the LED but provides a greater dispersion of light emitted from the taper 160.

Figure 6:
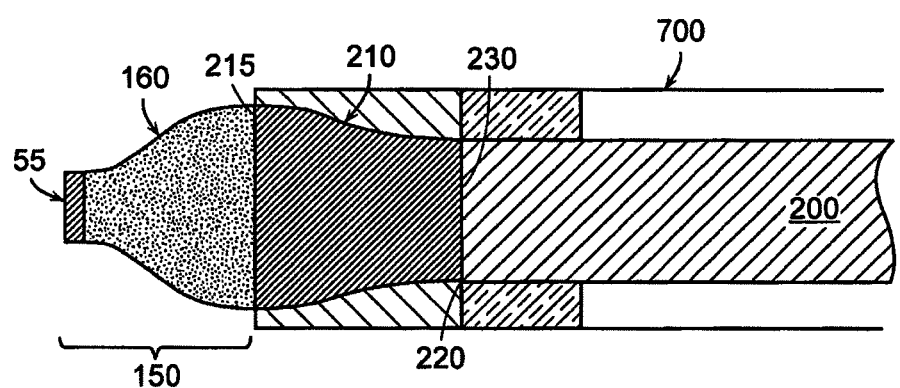
FIG. 6 is an illustration of another embodiment of an illumination device including a substantially planar light-emitting surface in accordance with the present invention.

Referring to FIG. 6, the illumination device 150 can be combined with a light guide bundle 200 including a light post taper 210. The illumination device 150 can be used as the light source for an endoscope. The light from the LED 55 is emitted through the illumination device 150 and is collected by the light post taper 210, which is adhered to the fiber optic light guide bundle 200. The light guide bundle 200 transmits the light to a remote location, such as, for example, through the body of the endoscope to illuminate an object under inspection. In general, the light post taper 210 selected for use with the illumination device 150 and the light guide bundle 200 has a first end or light receiving end 215 that has a surface area size comparable to the second end of the taper 160 and a second end or a light transmitting end 220 that has a surface area size comparable to the size of the connection end 230 of the light guide bundle 200.

Figure 7:
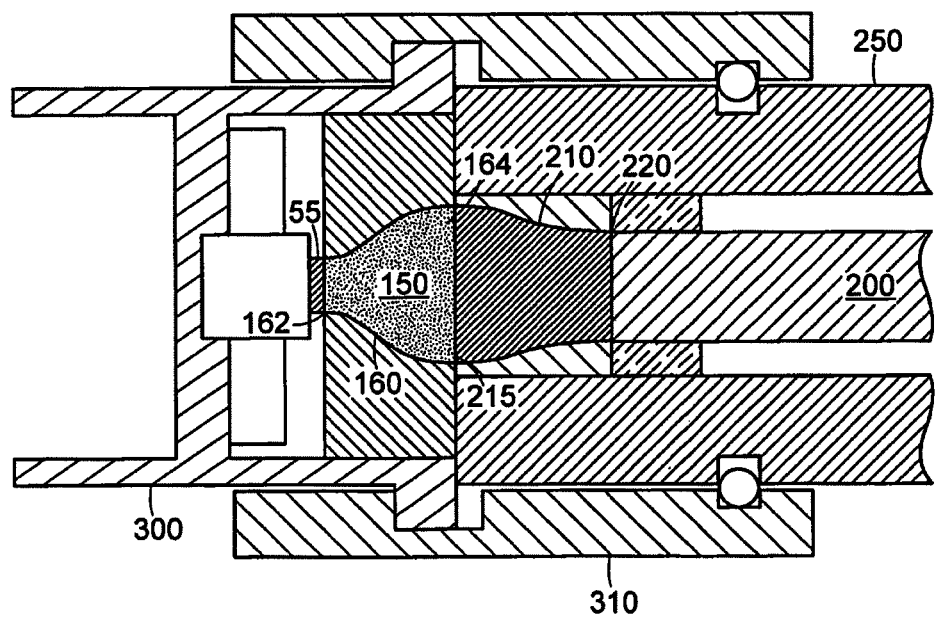
FIG. 7 is an illustration of the illumination device of FIG. 6 disposed within a handle of an endoscope.

In certain embodiments, the illumination device 150 can be positioned within a housing. Referring to FIG. 7, illumination device 150 is within a detachable light source housing 300 including a connector 310 to couple the illumination device 150 to a light guide post taper 210 surrounded by a light post 250. The illumination device 150, including the LED 55 having a light-emitting surface 65 proximate to taper 160, is inserted into a recess within the detachable housing 300. The light post 250 mates with one end of the detachable housing so that the light post taper 210 comes into direct contact with the taper 160 of the illumination device.

The optical taper 160 and the light post taper 210 can be selected for use with the illumination device 150 to increase the amount of light transmitted from the illumination device into the light guide bundle 200. For example, in an embodiment in which the optical taper 160 has a 1:3 ratio of end areas, with the small surface area end 162 having a 1.0 NA and a large surface area end 164 having a 0.33 NA, the collection angle at the small surface area end 162 is 180 degrees. The 1:3 ratio of end diameters cause the output NA to decrease to 0.33. In other words, the light exiting the larger surface area end 164 has an angular aperture of approximately 39 degrees. As a result, the light initially emitted by the LED 55 over the 180 degrees exits the taper 160 contained in a 39 degree cone at the larger surface area end 164. In the present embodiment, the light post taper 210 located proximate to the larger surface area end 164 is made of 0.66 NA glass and has a 2:1 diameter ratio. As a result, the larger surface area end 215 of the light post taper 210 receives light over about a 39 degree angle, a near perfect match to the light transmitted from the larger surface area end 164 of the optical taper 160. The light entering the light post taper 210 is reduced in diameter by a factor of 2, with a resulting increase in numerical aperture to 0.66 NA and an exit cone angle of 83 degrees for the light exiting the smaller surface area end 220 of the light post taper 210. Adhered directly to the smaller surface area end 220 of the light post taper 210 is the light guide bundle 200 formed of 0.66 NA glass, which has an acceptance angle (e.g., 83 degrees) that substantially matches the exit angle of the light post taper 210 (e.g., 83 degrees).

The illumination devices described above can be used to illuminate objects. For example, by utilizing either device 50 or 150, light from a light source can be collimated and transmitted to illuminate an object. Specifically, by coupling an optical rod or optical taper to a substantially planar light-emitting surface of an LED and activating the LED, the light generated and dispersed by the LED is collimated and transmitted through the optical rod and taper to produce a collimated light beam that can illuminate objects. In certain embodiments, the device 50 or 150 can be disposed within a lamp. When the lamp is positioned relative to an object and the light source 55 within the lamp is activated, the lamp produces a spot light which illuminates the object.

Figure 8:
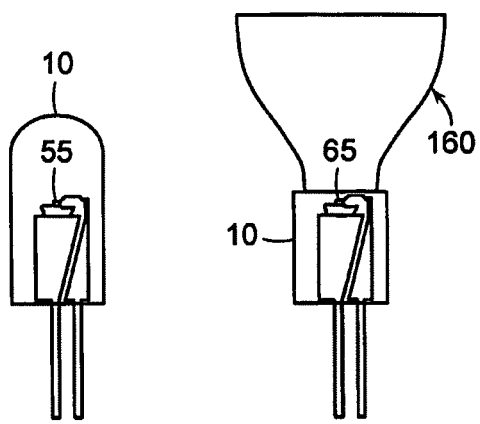
FIG. 8 is an illustration of another embodiment of an illumination device including a substantially planar light-emitting surface in accordance with the present invention.

While certain embodiments have been described, other embodiments are also possible. As an example, while LED 55 has been described as a chip 55 free from or removed completely from a dome lens, in some embodiments, such as the embodiment shown in FIG. 8, the LED 55 can remain in a modified or partially removed dome lens. Specifically, the dome lens 10 surrounding the LED 55 can be ground and polished nearly down to the level of the encapsulent-LED interface, so as to preserve the integrity of the mechanical package of the LED chip. After the dome lens has been partially removed, the planar light-emitting surface 65 of the LED 55 is accessible for connection to an end of the optical rod 60 or optical taper 160. To couple the optical rod or taper to the substantially planar light-emitting surface, a manufacturer positions an end of the rod or taper in a proximate relationship to the light-emitting surface 65. This process entails positioning the optical rod or taper as close as possible to the light-emitting surface 65 without damaging the light-emitting qualities of the LED 55. For example, in certain embodiments, the end of the rod or taper is in direct physical contact with the surface 65. In other embodiments, the end of the rod or taper is spaced a distance less than about 1 to 2 millimeters away from the surface 65. As a result, air, gas, adhesive, or an index matching material, such as, for example, a coupling gel may be disposed between the surface 65 and the end of the rod or taper within the 1 to 2 millimeter gap.

Variations, modifications, and other implementations of what is described herein will occur to those of ordinary skill without departing from the spirit and the scope of the invention. Accordingly, the invention is not to be defined only by the preceding illustrative description.

What is claimed is:

1. A detachable illumination system comprising:
   a housing that detachably mates with a light guide;
   an illumination device disposed within a recess in the housing, the illumination device including a substantially planar light-emitting surface of a light source of the illumination device which is proximate to a first end of an optical taper; and
   a light post taper, wherein a second end of the light post taper is coupled to a connection end of the light guide, and a second end of the optical taper is proximate to a first end of the light post taper when the housing mates with the light guide.

2. The detachable illumination system of claim 1, wherein the housing includes a mechanical connector that mates with the light guide.

3. The detachable illumination system of claim 1, wherein the illumination device includes a light-emitting diode chip.

4. The detachable illumination system of claim 3, wherein the light-emitting diode chip has a power consumption of about 1 to 5 W.

5. The detachable illumination system of claim 3, wherein the substantially planar light-emitting surface comprises a flat transparent window disposed above the light-emitting diode chip.

6. The detachable illumination system of claim 3, wherein the substantially planar light-emitting surface comprises an emitting surface of the light-emitting diode chip coated with a film of a substance that emits light when the light-emitting diode chip is activated.

7. The detachable illumination system of claim 1, wherein the illumination device includes a taper in direct contact with the substantially planar light-emitting surface.

8. The detachable illumination system of claim 1, wherein an adhesive or an index matching material is disposed between the substantially planar light-emitting surface and the optical taper.

9. The detachable illumination system of claim 2 wherein the first end of the light post taper is a larger surface area of the light post taper and the second end of the light post taper is a smaller surface area end of the light post taper.

10. A detachable illumination system comprising:
    a housing that detachably mates with a light guide disposed within an endoscope;
    an illumination device disposed within a recess in the housing, the illumination device including a substantially planar light-emitting surface of a light source of the illumination device which is proximate to an optical taper; and
    a light post taper, wherein a second end of the light post taper is coupled to a connection end of the light guide, and a second end of the optical taper is proximate to a first end of the light post taper when the housing mates with the light guide.

11. The detachable illumination system of claim 10, wherein the housing includes a mechanical connector that mates with the light guide.

12. The detachable illumination system of claim 10, wherein the illumination device includes a light-emitting diode chip.

13. The detachable illumination system of claim 12, wherein the substantially planar light-emitting surface comprises a flat transparent window disposed above the light-emitting diode chip.

14. The detachable illumination system of claim 12, wherein the substantially planar light-emitting surface comprises an emitting surface of the light-emitting diode chip coated with a film of a substance that emits light when the light-emitting diode chip is activated.

15. The detachable illumination system of claim 10, wherein the illumination device includes a taper in direct contact with the substantially planar light-emitting surface.

16. The detachable illumination system of claim 10, wherein an adhesive or an index matching material is disposed between the substantially planar light-emitting surface and the optical taper.

* * * * *